United States Patent
Lee et al.

(10) Patent No.: US 11,690,727 B2
(45) Date of Patent: Jul. 4, 2023

(54) ARTIFICIAL ANKLE JOINT TIBIA COMPONENT

(71) Applicants: CORENTEC CO., LTD., Cheonan-si (KR); CHONNAM NATIONAL UNIVERSITY HOSPITAL, Gwangju (KR); INDUSTRY FOUNDATION OF CHONNAM NATIONAL UNIVERSITY, Gwangju (KR)

(72) Inventors: Keun-Bae Lee, Gwangju (KR); Tae-Jin Shin, Hanam-si (KR)

(73) Assignees: CORENTEC CO., LTD., Chungcheongnam-do (KR); CHONNAM NATIONAL UNIVERSITY HOSPITAL, Gwangju (KR); INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 221 days.

(21) Appl. No.: 16/642,795

(22) PCT Filed: Aug. 28, 2018

(86) PCT No.: PCT/KR2018/009917
§ 371 (c)(1),
(2) Date: Feb. 27, 2020

(87) PCT Pub. No.: WO2019/045412
PCT Pub. Date: Mar. 7, 2019

(65) Prior Publication Data
US 2020/0188126 A1    Jun. 18, 2020

(30) Foreign Application Priority Data
Aug. 29, 2017    (KR) .......................... 10-2017-0109179

(51) Int. Cl.
*A61F 2/42*    (2006.01)
*A61F 2/30*    (2006.01)

(52) U.S. Cl.
CPC .. *A61F 2/4202* (2013.01); *A61F 2002/30884* (2013.01); *A61F 2002/4205* (2013.01)

(58) Field of Classification Search
CPC .......... A61F 2/4202; A61F 2002/30884; A61F 2002/4205; A61F 2002/30878
See application file for complete search history.

(56) References Cited

U.S. PATENT DOCUMENTS

| | | | |
|---|---|---|---|
| 5,480,445 A * | 1/1996 | Burkinshaw ............ | A61F 2/389 623/20.32 |
| 6,409,767 B1 * | 6/2002 | Perice ................... | A61F 2/4202 623/21.18 |

(Continued)

FOREIGN PATENT DOCUMENTS

| JP | 2001-161728 A | 6/2001 |
|---|---|---|
| JP | 2008-104884 A | 5/2008 |

(Continued)

OTHER PUBLICATIONS

International Search Report dated Dec. 6, 2018, issued in PCT Application No. PCT/KR2018/009917, filed Aug. 28, 2018.

(Continued)

*Primary Examiner* — Marcia L Watkins
(74) *Attorney, Agent, or Firm* — Workman Nydegger

(57) ABSTRACT

The present disclosure relates to an artificial ankle joint tibial component and, more particularly, to an artificial ankle joint tibial component of an implant that is implanted into a body, the implant including: a body part having a contact surface in contact with a resected surface of a distal end of a tibia of a joint and a joint surface facing a joint; and a fixing part formed to extend a predetermined length upwards from the contact surface, wherein the fixing part is config- (Continued)

ured as a single body formed to extent a predetermined length upwards from the center in the front area of the contact surface and includes a wing extending to one side, and wherein the wing includes at least one posterior wing that extends at a predetermined angle relative to an AP line, thereby preventing stress from being concentrated on one wing to avoid a fracture thereof and increasing the contact area between a bone and an implant to strengthen fixing force, prevent rotation, and disperse stress, so that bone resorption around the wing can be prevented.

18 Claims, 9 Drawing Sheets

(56) References Cited

U.S. PATENT DOCUMENTS

| | | | |
|---|---|---|---|
| 7,323,012 B1 | 1/2008 | Stone | |
| 8,043,375 B2* | 10/2011 | Strzepa | A61F 2/30756 |
| | | | 623/16.11 |
| 8,900,316 B2* | 12/2014 | Lenz | A61F 2/389 |
| | | | 623/20.14 |
| 9,610,168 B2 | 4/2017 | Terrill et al. | |
| 11,013,607 B2* | 5/2021 | Pak | A61F 2/30749 |
| 2004/0225367 A1* | 11/2004 | Glien | A61F 2/4003 |
| | | | 623/19.14 |
| 2005/0261775 A1* | 11/2005 | Baum | A61F 2/4081 |
| | | | 623/19.12 |
| 2008/0103603 A1* | 5/2008 | Hintermann | A61F 2/4606 |
| | | | 623/20.32 |
| 2012/0330429 A1* | 12/2012 | Axelson, Jr. | A61F 2/30771 |
| | | | 623/20.19 |
| 2014/0257507 A1* | 9/2014 | Wang | A61F 2/461 |
| | | | 623/20.34 |
| 2015/0045902 A1 | 2/2015 | Perler | |
| 2015/0320567 A1* | 11/2015 | Terrill | A61F 2/4202 |
| | | | 623/21.18 |
| 2017/0312084 A1* | 11/2017 | Ferro | A61F 2/30771 |
| 2021/0220143 A1* | 7/2021 | Leemrijse | A61F 2/4202 |

FOREIGN PATENT DOCUMENTS

| | | |
|---|---|---|
| JP | 2017-501013 A | 1/2017 |
| JP | 2017-515577 A | 6/2017 |

OTHER PUBLICATIONS

Written Opinion dated Dec. 6, 2018, issued in PCT Application No. PCT/KR2018/009917, filed Aug. 28, 2018.

* cited by examiner

Prior Art

ARTIFICIAL ANKLE JOINT TIBIA COMPONENT

BACKGROUND OF THE INVENTION

1. Field of the Invention

The present disclosure relates to an artificial ankle joint tibial component and, more particularly, to an implant that is implanted into a body, which includes: a body part having a contact surface in contact with a resected surface of a joint surface of a distal end of a tibia and a joint surface facing a joint; and a fixing part formed to extend a predetermined length upwards from the contact surface, wherein the fixing part is configured as a single body formed to extend a predetermined length upwards from the center in the anterior area of the contact surface and includes a wing extending to one side, and wherein the wing includes at least one posterior wing that extends at a predetermined angle relative to an AP line, thereby preventing stress from being concentrated on one wing to avoid a fracture thereof and increasing the contact area between a bone and an implant to strengthen fixing force, prevent rotation, and distribute stress, so that bone resorption around the wing can be prevented.

2. Description of the Prior Art

In the case where the ankle joint fails to function due to various causes such as degenerative arthritis, post-traumatic arthritis, rheumatoid arthritis, and the like of the ankle, ankle arthroplasty is performed using an artificial ankle joint. Artificial ankle joint arthroplasty, which started in the 1970s, showed clinic results that did not meet expectations because the surgery procedure was highly complicated and many complications occurred in early stages. Therefore, artificial ankle joint arthroplasty tended to be avoided, and most treatments were made using an ankle fixation procedure. However, the development of replacements and the development of surgical methods according to the advancement of science have brought about satisfactory mid- and long-term results, so that artificial ankle joint arthroplasty is widely used today.

This artificial ankle joint includes several components, and primarily includes a tibial prosthesis coupled to a tibia, a talus prosthesis coupled to a talus, and a polyethylene insert acting as a bearing by connecting the above two components. In addition, a three-component mobile-bearing in which the tibial prosthesis and the insert, among the components, are separated is the most widely used type in the world.

PRIOR PATENT

U.S. Pat. No. 9,610,168 (2017 Mar. 15. Registration) "Total Ankle Replacement Prosthesis"

The disclosure shown in the patent document discloses an artificial ankle joint implant for replacing an ankle joint. In particular, a tibial implant coupled to the distal end of the tibia includes two pegs in the front of the surface in contact with the tibia, which are inserted into a resected surface of the tibia, thereby providing a strong fixing force. By employing a total of two pegs each provided on each side as described above, it is possible to accurately insert the tibial implant and to prevent the implant from being rotated and dislocated by external force or the like even after insertion. In addition, there is an advantage in that stable fixation can be made early in the postoperative period by improving the bonding force between the implant and the bone.

The tibial implant according to the prior art are shown in FIGS. 1 and 2. Referring to FIG. 1, the tibial implant (T) has a total of two pegs (A) each provided on each side for connection with the tibia. In addition, according to the prior art, there are tibial implants having three or more pegs, as well as the tibial implant disclosed in the patent document and shown in FIGS. 1 and 2.

However, since the above tibial implants according to the prior art include two or more pegs, stress is concentrated on the pegs, and the portion between the pegs fail to appropriately support a load, thereby causing a stress shielding effect.

The above-mentioned effect, also called a "stress blocking effect", refers to a phenomenon in which the stress is concentrated on a specific portion, and thus the force cannot be properly transmitted to the peripheral portions thereof. The stress shielding effect is primarily caused in the case where the shapes of the implant and bone do not correspond to each other or the case where there is a difference in the strain of the load between the implant and the bone due to the difference in the modulus of elasticity therebetween even if the implant is correctly inserted, so that the force is concentrated on a specific portion.

Since the tibial implant according to the prior art has two or more pegs spaced a predetermined distance apart from each other, the stress generated by the load of the human body, the motion of muscles, or the like is concentrated on the pegs, whereas the stress cannot be appropriately transmitted to the bones located therebetween.

More specifically, referring to FIG. 2, the stress is concentrated in the pegs (A) in the state in which the tibial implant (T) is inserted, and the tibia located in a portion (H) between the two pegs (A) is not applied with an appropriate stress and is not subject to force.

When the stress shielding effect occurs, the bone corresponding thereto is subject to bone resorption, thereby lowering the density of the bone and weakening the strength thereof.

Bone resorption denotes a phenomenon in which the density and strength of the bone are lowered by losing calcium from bone tissues by osteoclasts, and is an essential procedure consistently occurring even in a healthy body for bone regeneration. However, if the stress shielding effect occurs after implantation of an implant, Wolff's Law causes excessive bone resorption in the bone to which no force is applied.

Wolff's Law states that bones of humans and animals change in a shape and density in response to external force, and thus bone resorption is actively performed in the bone in a portion on which no force acts, resulting in lower density and strength of the bone.

As described above, the tibial implant according to the prior art fails to transmit force to the bone located between a plurality of pegs. Therefore, the density and strength of the bone at the corresponding position become lower due to bone resorption with time. As a result, the risk of weakening the fixing force of the implant is increased, thereby reducing the long-term survival rate of the artificial ankle joint.

Therefore, there is a need for a tibial implant having a structure capable of improving initial fixing force while reducing bone resorption around the pegs by attenuating the stress shielding effect due to a plurality of pegs.

In general, revision arthroplasty must be performed on the artificial joint after a certain period of time. However, removal of existing cemented implants for revision arthroplasty results in significant bone loss around the coupling portion. In the case of a cement-free implant developed to compensate for the cemented implant, since a plurality of pegs is provided in order to increase fixing force, the bone loss resulting from the removal of the implant is not small.

That is, the tibial implants having two or more pegs according to the prior art have a problem in that the bone located between the pegs is removed together when removing an existing implant for revision arthroplasty.

This is also illustrated in FIG. 2. When the pre-implanted tibial implant (T) is removed for revision arthroplasty, most of the bones in a portion (B) including the portion (H) between the both pegs (A) are removed. If the bone is removed in such an enormous range, there is not enough bone left, which makes it difficult to execute revision arthroplasty.

Therefore, there is a need for a tibial implant having a structure capable of minimizing bone loss when removing the implant for revision arthroplasty and preventing an axis from twisting during insertion while reducing the burden on a surgeon and securing the initial fixing force.

Artificial joints, especially artificial ankle joints, may cause heterotopic ossification in which unnecessary bones are generated if the resected surface of the bone is exposed after an operation.

Heterotopic ossification indicates that bone tissues are formed in abnormal portions, and often occurs around the joints. If heterotopic ossification occurs after the artificial ankle joint arthroplasty, the bones grow around the implant to cause joint pain and reduce joint motion, which may lead to loss of a function of the artificial joint. This heterotopic ossification usually occurs in the posterior of the joint.

The occurrence rate of heterotopic ossification after artificial ankle joint arthroplasty is reported to be different according to surgeons, but is usually about 25%. In particular, recent research results have reported that the heterotopic ossification is accompanied by symptoms in about 5% of patients, thereby limiting the range of motion of a joint and causing severe pain in the joints, so that the function of the artificial joint significantly deteriorates. In order to resolve this inconvenience, a surgical method of removing the generated bones is required, which further imposes a burden of reoperation on the patient.

Therefore, an implant having an improved posterior structure to prevent heterotopic ossification after artificial ankle joint arthroplasty is required.

SUMMARY OF THE INVENTION

The present disclosure has been made to solve the above problems and has an objective to provide an implant having a structure capable of strengthening the fixing force with the bones and evenly distributing the stress to prevent bone resorption due to the stress shieling effect, thereby increasing the life span thereof and reducing development of complications.

In addition, another objective of the present disclosure is to provide an implant capable of minimizing the amount of bone to be removed when performing revision arthroplasty to facilitate an operation and reduce the burden on the surgeon.

In addition, another objective of the present disclosure is to provide an implant capable of preventing an axis from being twisted and inserted into the bone and increasing the rotational resistance after insertion to prevent dislocation thereof from the position, thereby facilitating an operation and alleviating the burden from the surgeon and the patient.

In addition, another objective of the present disclosure is to provide an implant that can be easily inserted into the bone to shorten the operation time, thereby reducing the burden of the surgeon and improving the health recovery of the patient.

In addition, another objective of the present disclosure is to provide an implant that prevents the stress from being concentrated on one side of the implant to be broken, thereby extending the life span of the artificial joint and reducing the pain and burden of the patient.

In addition, another objective of the present disclosure is to provide an implant capable of shortening the recovery time of the patient by securing the initial fixing force, thereby reducing the burden of the patient.

In addition, another objective of the present disclosure is to provide an implant that can be easily coupled to the tibia, prevents bone resorption due to the stress shielding effect to prolong the life span of the artificial ankle joint, prevents fractures to reduce the pain and burden of the patient, and increases the amount of preserved bone in revision arthroplasty, thereby reducing the burden of the surgeon.

Further, another objective of the present disclosure is to provide an implant having a structure that includes a blocking part extending a predetermined length upwards from the posterior of a body part to prevent heterotopic ossification in which a bone grows in the posterior of the tibia after an operation, thereby increasing the life span of the artificial joint, relieving the pain of the patient, and securing a sufficient moving range.

The present disclosure is implemented by embodiments having the following configuration in order to attain the above objectives.

According to an embodiment of the present disclosure, in an artificial ankle joint tibial component according to the present disclosure, an implant that is implanted into a body may include: a body part having a contact surface in contact with a resected surface of a distal end of a tibia and a joint surface facing a joint; and a fixing part extending a predetermined length upwards from the contact surface, wherein the fixing part may be configured to have a form so as to be inserted into the bone, thereby strengthening fixing force and preventing bone absorption by distributing stress.

According to another embodiment of the present disclosure, in the artificial ankle joint tibial component according to the present disclosure, the fixing part may be configured as a single body formed to extend a predetermined length upwards from the contact surface so as to facilitate insertion thereof into the bone and minimize the amount of bone to be removed in revision arthroplasty.

According to another embodiment of the present disclosure, in the artificial ankle joint tibial component according to the present disclosure, the fixing part may include a wing extending to one side to increase the rotational resistance when the fixing part is inserted into the bone, thereby preventing the same from being separated from a correct position.

According to another embodiment of the present disclosure, in the artificial ankle joint tibial component according to the present disclosure, the wing may include at least one posterior wing extending at a predetermined angle relative to an AP line to prevent stress from being concentrated on one wing, thereby preventing a fracture.

According to another embodiment of the present disclosure, in the artificial ankle joint tibial component according to the present disclosure, the wing may include at least two posterior wings extending at angles in different directions from each other on the basis of an AP line to prevent stress from being concentrated on one wing, thereby preventing a fracture.

According to another embodiment of the present disclosure, in the artificial ankle joint tibial component according to the present disclosure, the posterior wings have angles symmetrical with each other on the basis of the AP line.

According to another embodiment of the present disclosure, in the artificial ankle joint tibial component according to the present disclosure, the wing may further include anterior wings that are symmetrical with the posterior wings on the basis of an ML line.

According to another embodiment of the present disclosure, in the artificial ankle joint tibial component according to the present disclosure, the anterior wing and the posterior wing are formed at 90 degrees from each other.

According to another embodiment of the present disclosure, in the artificial ankle joint tibial component according to the present disclosure, the fixing part may have a tapered shape overall in which the cross-sectional area thereof is reduced as it goes from the contact surface to the top end, thereby facilitating insertion thereof into the bone and improving fixing force.

According to another embodiment of the present disclosure, in the artificial ankle joint tibial component according to the present disclosure, at least a portion of the wing may have a tapered shape in the vertical direction in which the width thereof is reduced as it goes from the contact surface to a top end.

According to another embodiment of the present disclosure, in the artificial ankle joint tibial component according to the present disclosure, at least a portion of the wing may have a tapered shape in which the length thereof is reduced as it goes from the contact surface to a top end, thereby facilitating insertion thereof into the bone and improving fixing force.

According to another embodiment of the present disclosure, in the artificial ankle joint tibial component according to the present disclosure, a portion in which a side surface of the fixing part is connected to the contact surface is formed to have a gentle curved surface to support a load and distribute stress, thereby preventing a fracture.

According to another embodiment of the present disclosure, in the artificial ankle joint tibial component according to the present disclosure, a portion in which the side surface of the fixing part is connected to the top end is formed to have a gentle curved surface to facilitate insertion thereof into the bone.

According to another embodiment of the present disclosure, in the artificial ankle joint tibial component according to the present disclosure, a portion in which two neighboring wings meet on the side surface of the fixing portion is formed to have a gentle curved surface to enable a natural connection and support a load.

According to another embodiment, in the artificial ankle joint tibial component according to the present disclosure, the fixing part may be formed to extend a predetermined length upwards at a predetermined angle toward the posterior thereof, thereby facilitating insertion thereof into the bone.

According to another embodiment, in the artificial ankle joint tibial component according to the present disclosure, the implant may further include a spike in the form of a horn, which is disposed in the posterior of the contact surface, so as to strengthen fixing force to the bone.

According to another embodiment, in the artificial ankle joint tibial component according to the present disclosure, a boundary portion between the spike and the contact surface has a boundary surface, which is a gentle curved surface connecting the same, to support a load and distribute stress, thereby preventing fracture.

According to another embodiment, in the artificial ankle joint tibial component according to the present disclosure, the implant may be a tibial implant that is coupled to a tibia in artificial ankle joint arthroplasty.

According to another embodiment, in the artificial ankle joint tibial component according to the present disclosure, the lateral surface of the implant may be formed to be a concave curved surface.

According to another embodiment, in the artificial ankle joint tibial component according to the present disclosure, an implant that is implanted into a body may include: a body part having a contact surface in contact with a resected surface of a distal end of a tibia and a joint surface facing a joint; a fixing part extending a predetermined length upwards from the contact surface; and a blocking part extending a predetermined length upwards from the posterior of the body part.

According to another embodiment, in the artificial ankle joint tibial component according to the present disclosure, the blocking part may be formed along a posterior boundary surface of the body part to prevent heterotopic ossification.

The present disclosure can give the following effects by the above embodiments, configurations, combinations, and usage relationship, which will be described below.

The present disclosure has the effect of strengthening the fixing force with the bones and evenly distributing the stress to prevent bone resorption due to the stress spieling effect, thereby increasing the life span thereof and reducing the pain and burden of the patient by preventing a fracture.

In addition, the present disclosure has the effect of minimizing the amount of bone to be removed when performing revision arthroplasty to facilitate the operation and reduce the burden on the surgeon.

In addition, the present disclosure has the effect of preventing an axis from being twisted and inserted into the bone and increasing the rotational resistance to prevent dislocation thereof from the position, thereby facilitating the operation and alleviating the burden from the surgeon and the patient.

In addition, the present disclosure has the effect of reducing the burden of the surgeon and improving the health recovery of the patient by shortening the operation time because the implant can be easily inserted into the bone.

In addition, the present disclosure has the effect of extending the life span of the artificial joint and relieving the pain and burden of the patient by preventing the stress from being concentrated on a specific portion of the implant to be broken.

In addition, the present disclosure has the effect of shortening the recovery time of the patient by securing the initial fixing force, thereby reducing the burden of the patient.

In addition, the present disclosure has the effect of being easily coupled to the tibia, preventing bone resorption due to the stress shielding effect to prolong the life span of the artificial ankle joint, preventing fractures to reduce the pain and burden of the patient, and increasing the amount of preserved bone in revision arthroplasty, thereby reducing the burden of the surgeon.

Further, the present disclosure has the effect of preventing heterotopic ossification in which a bone grows in the posterior of the tibia after the procedure by including a blocking part extending a predetermined length upwards from the posterior of the body part, thereby increasing the life span of the artificial joint, relieving the pain of the patient, and securing a sufficient moving range.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION OF THE EXEMPLARY EMBODIMENTS

Figure 1:
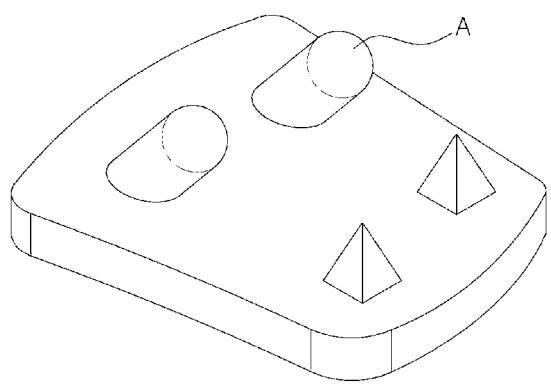
FIG. 1 is a perspective view showing a tibial implant according to the prior art.

Hereinafter, an artificial ankle joint tibial component according to the present disclosure will be described in detail with reference to the accompanying drawings. It should be noted that the same components in the figures are represented by the same reference numerals wherever possible. In addition, detailed descriptions of well-known functions and configurations that may unnecessarily obscure the subject matter of the present disclosure will be omitted. Unless otherwise defined, all terms in this specification are equivalent to the general meanings of the terms understood by those of ordinary skill in the art to which the present disclosure pertains, and if the terms conflict with the meanings of the terms used herein, they follow the definition used in the present specification.

Now, an artificial ankle joint tibial component of the present disclosure will be described in detail with reference to the accompanying drawings.

Figure 2:
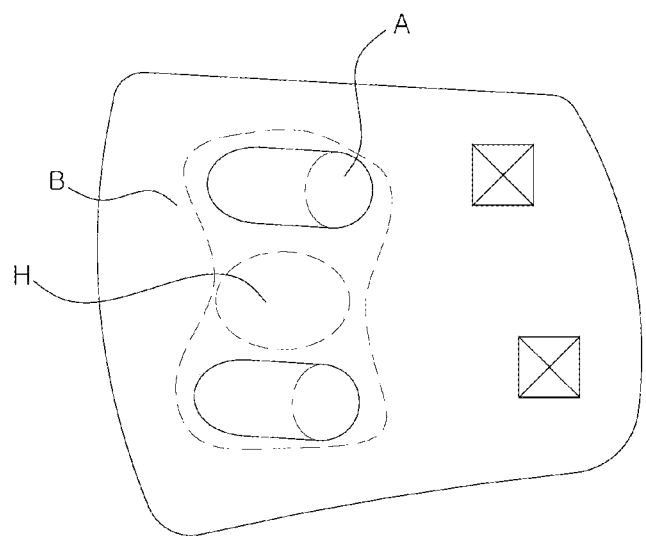
FIG. 2 is a plan view showing a tibial implant according to the prior art.
Figure 3:
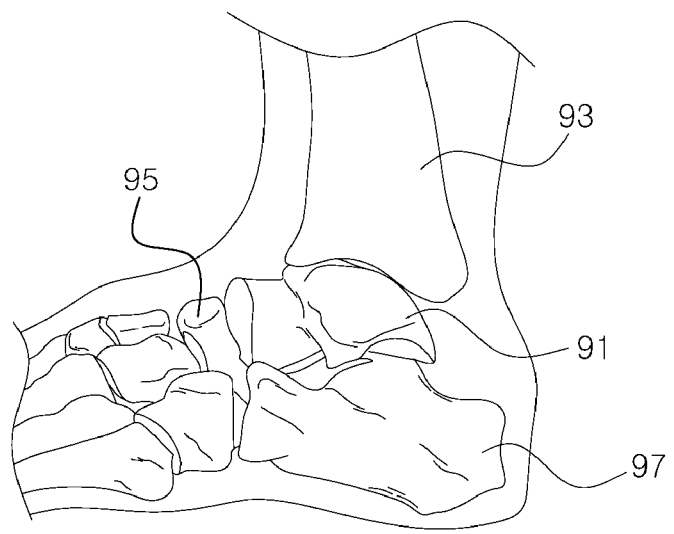
FIG. 3 is a side view showing the anatomical shape of an ankle joint for implantation of an implant.
Figure 4:
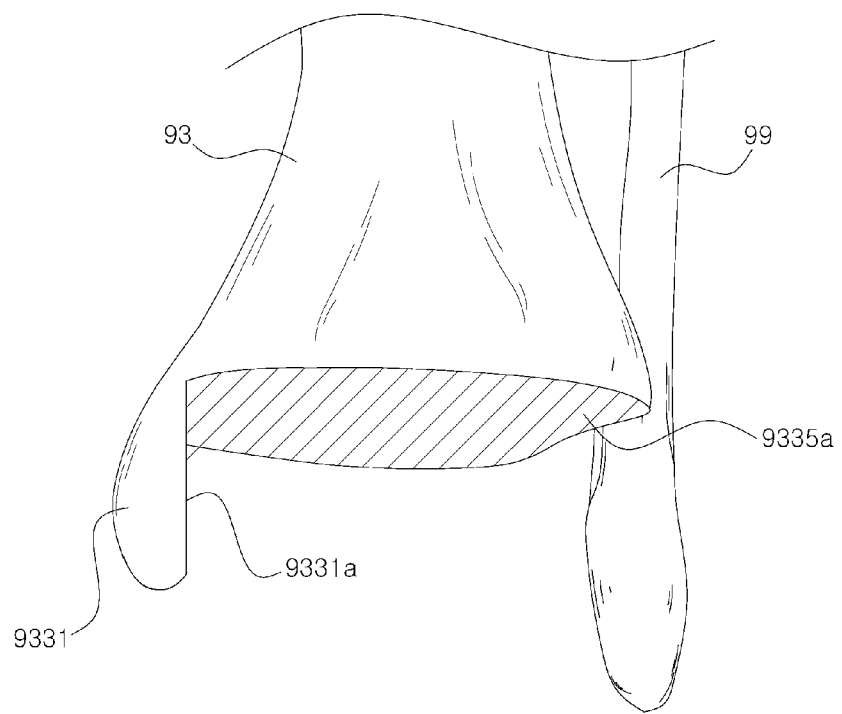
FIG. 4 is a perspective view showing the state of cutting a joint surface of a distal end of a tibia for implantation of an implant.
Figure 5:
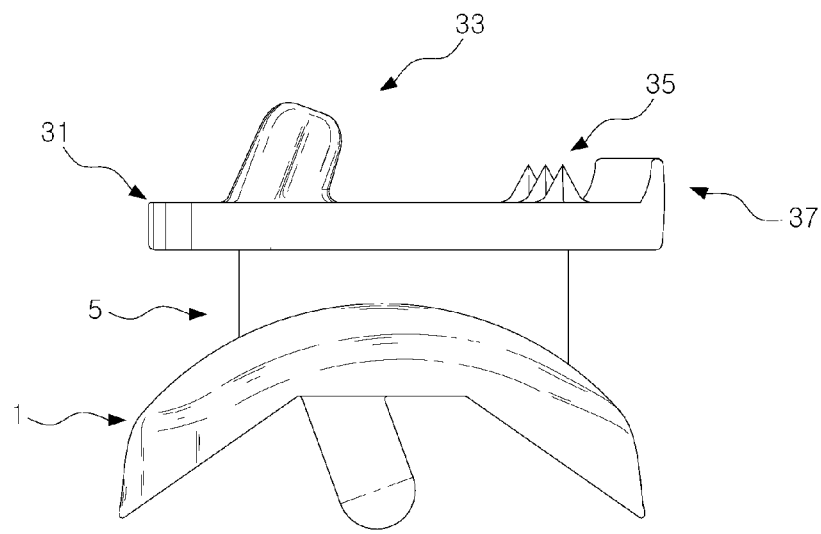
FIG. 5 is a side view showing the state in which a tibial implant is coupled to a talus implant and a bearing according to an embodiment of the present disclosure.
Figure 6:
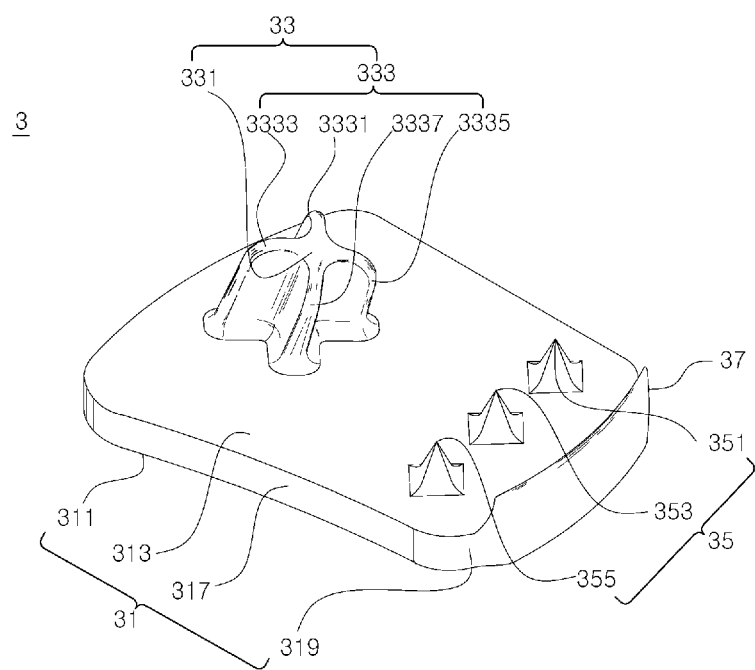
FIG. 6 is a perspective view showing a tibial implant according to an embodiment of the present disclosure.
Figure 7:
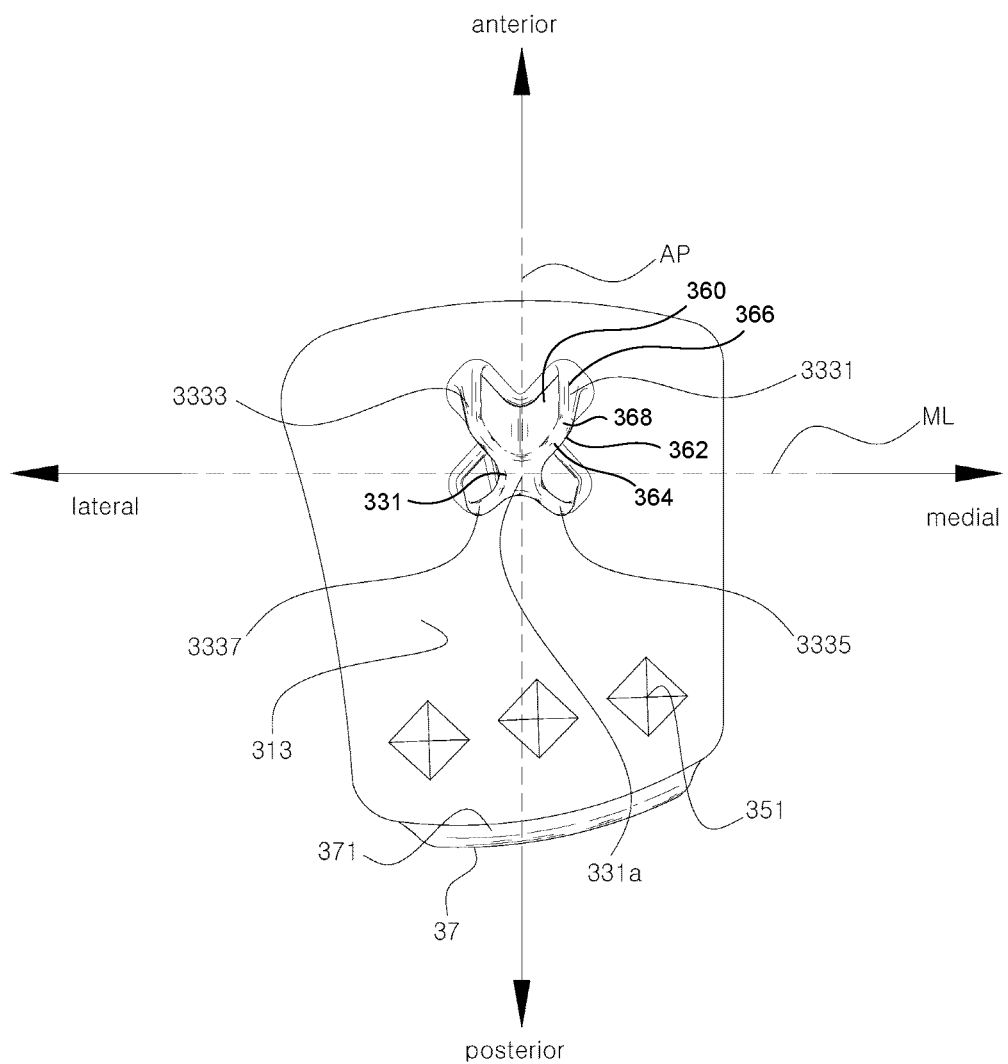
FIG. 7 is a plan view showing a tibial implant according to an embodiment of the present disclosure.
Figure 8:
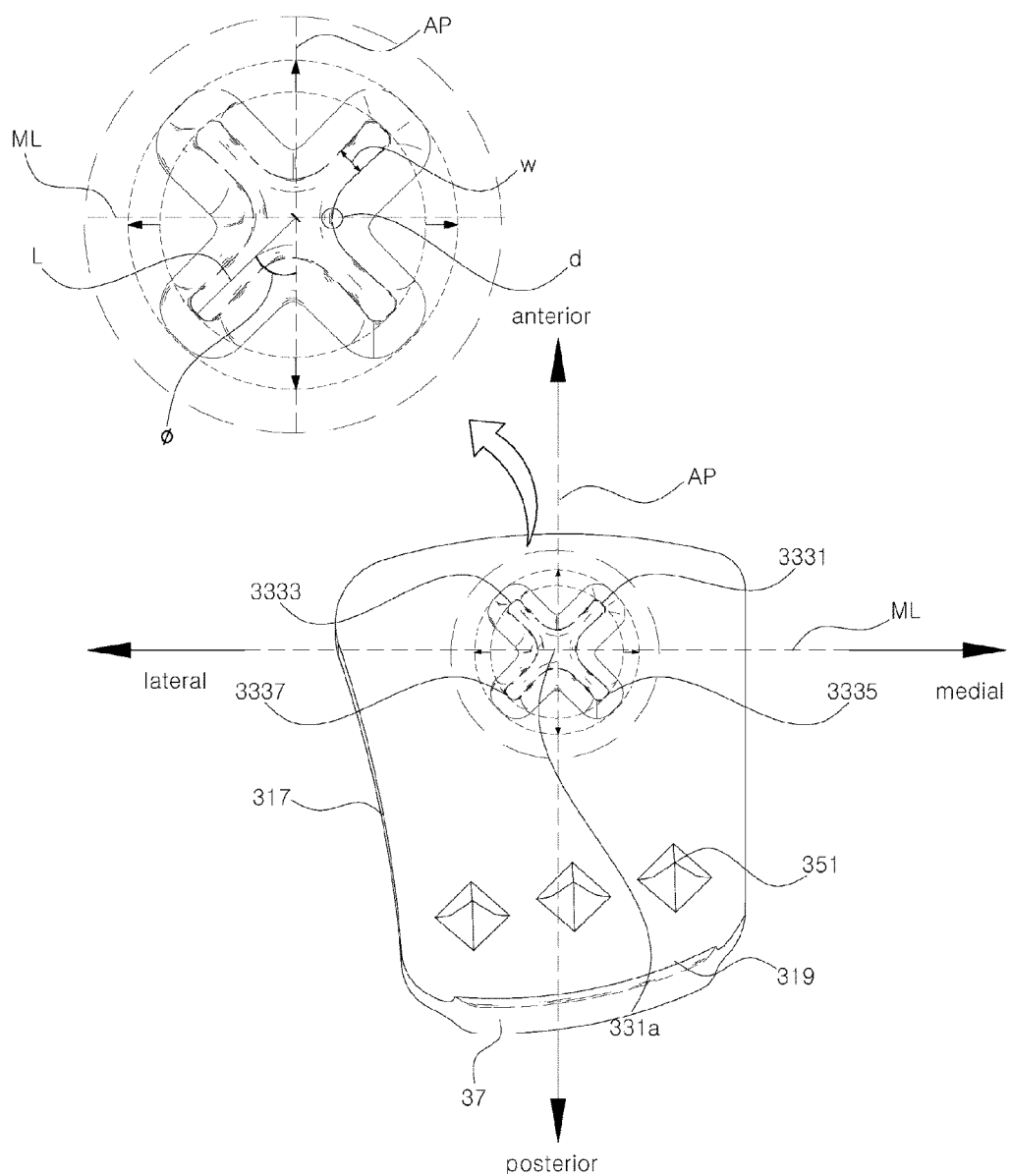
FIG. 8 is a plan view showing a tibial implant on the basis of a top surface of the tibial implant axis according to an embodiment of the present disclosure.
Figure 9:
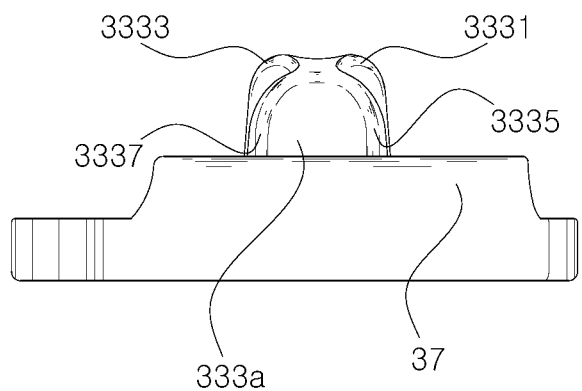
FIG. 9 is a rear view showing a tibial implant according to an embodiment of the present disclosure.
Figure 10:
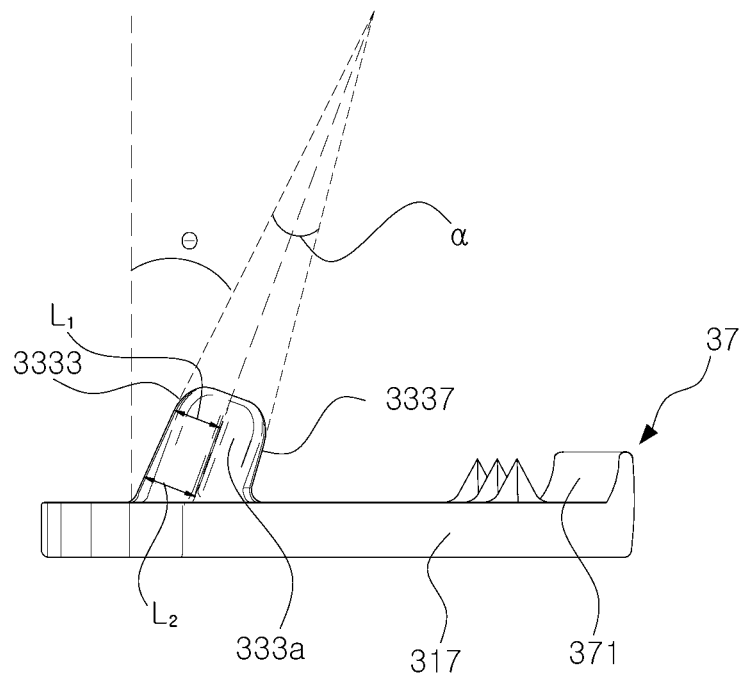
FIG. 10 is a side view showing a tibial implant according to an embodiment of the present disclosure.
Figure 11:
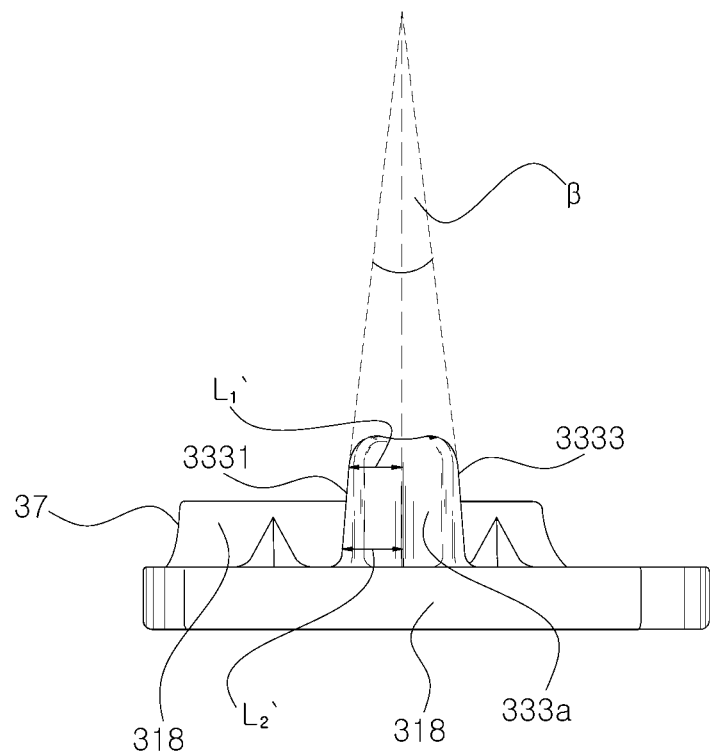
FIG. 11 is a front view showing a tibial implant according to an embodiment of the present disclosure.
Figure 12:
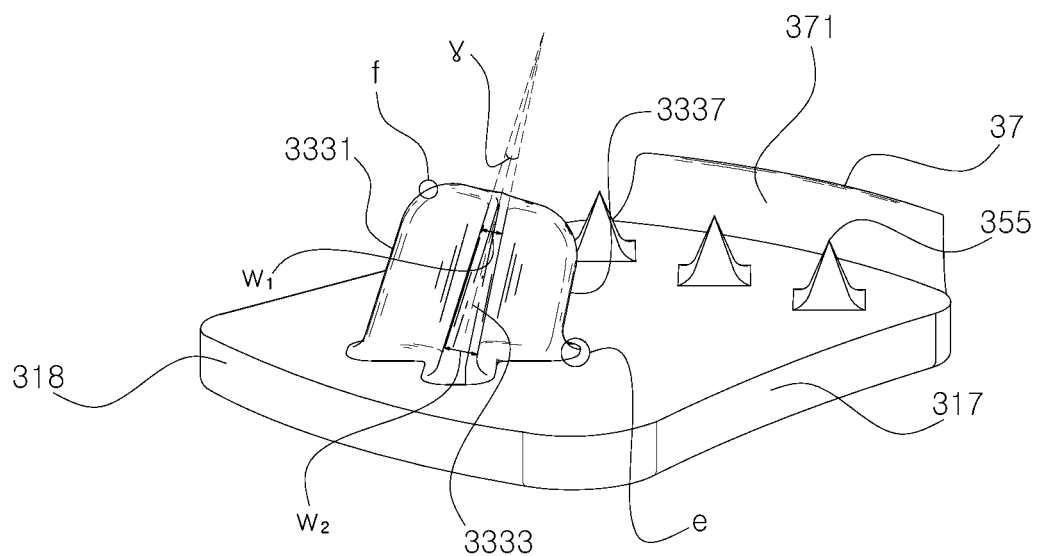
FIG. 12 is a perspective view showing a tibial implant according to an embodiment of the present disclosure.
Figure 13:
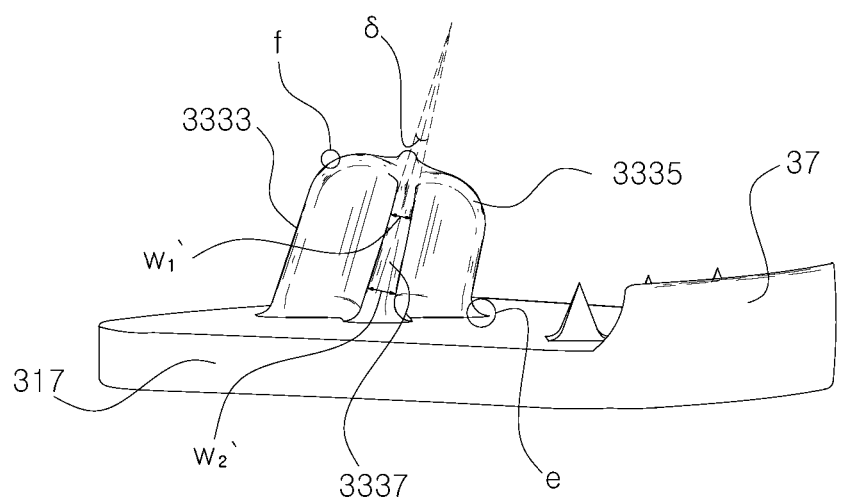
FIG. 13 is a perspective view illustrating a tibial implant according to an embodiment of the present disclosure.
Figure 14:
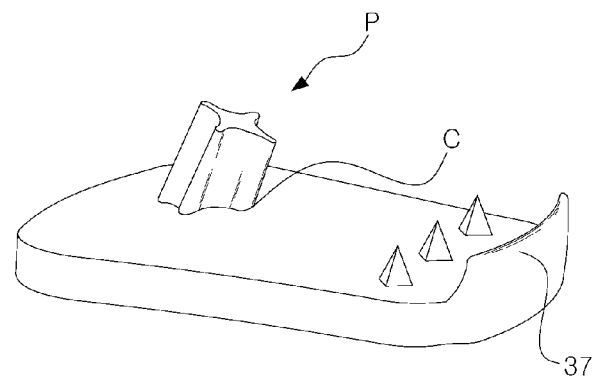
FIG. 14 is a perspective view showing a tibial implant according to another embodiment of the present disclosure.
Figure 15:
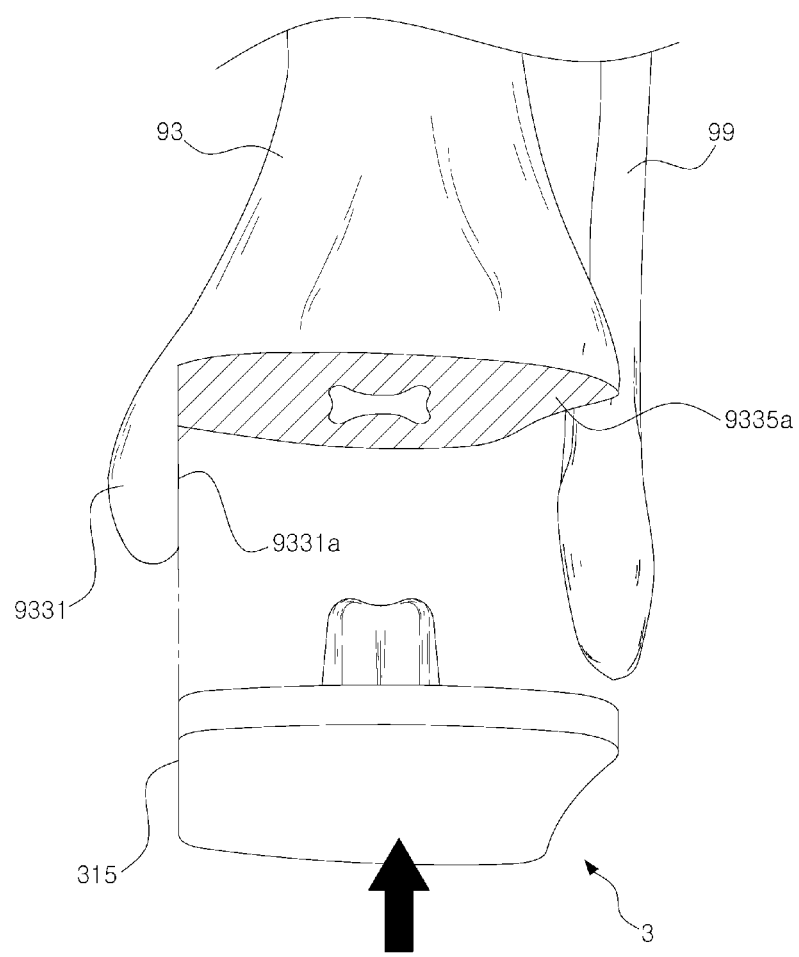
FIG. 15 is a perspective view illustrating a process in which a tibial implant is coupled to a resected surface of a tibia according to an embodiment of the present disclosure.

FIG. 1 is a perspective view showing a tibial implant according to the prior art; FIG. 2 is a plan view showing a tibial implant according to the prior art; FIG. 3 is a side view showing the anatomical shape of an ankle joint for implantation of an implant; FIG. 4 is a perspective view showing the state of cutting a joint surface of a distal end of a tibia for implantation of an implant; FIG. 5 is a side view showing the state in which a tibial implant is coupled to a talus implant and a bearing according to an embodiment of the present disclosure; FIG. 6 is a perspective view showing a tibial implant according to an embodiment of the present disclosure; FIG. 7 is a plan view showing a tibial implant according to an embodiment of the present disclosure; FIG. 8 is a plan view showing a tibial implant on the basis of a top surface of the tibial implant axis according to an embodiment of the present disclosure; FIG. 9 is a rear view showing a tibial implant according to an embodiment of the present disclosure; FIG. 10 is a side view showing a tibial implant according to an embodiment of the present disclosure; FIG. 11 is a front view showing a tibial implant according to an embodiment of the present disclosure; FIG. 12 is a perspective view showing a tibial implant according to an embodiment of the present disclosure; FIG. 13 is a perspective view illustrating a tibial implant according to an embodiment of the present disclosure; FIG. 14 is a perspective view showing a tibial implant according to another embodiment of the present disclosure; and FIG. 15 is a perspective view illustrating a process in which a tibial implant is coupled to a resected surface of a tibia according to an embodiment of the present disclosure.

First, the anatomical structure of an ankle into which an artificial ankle joint including a tibial implant 3 is implanted and the state of cutting the tibia will be described with reference to FIGS. 3 and 4.

FIG. 3 is a side view showing a distal end of a tibia (shinbone) 93 in an ankle joint (a fibula is not shown for the convenience). The tibia 93 is located on a talus 91, and the talus 91 is located between the tibia 93, a navicular 95, and a calcaneus (heel bone) 97. The tibia 93 moves forward and backward on the fornix of the talus, which is a proximal end of the talus 91, thereby performing dorsiflexion and plantar flexion motions. In performing artificial ankle joint arthroplasty, a talus implant 1 is implanted by cutting the fornix of the talus 91, and a tibial implant 3 is implanted by cutting a portion of the distal end of the tibia 93. Then, an insert 5 serving as a bearing is inserted between the two implants 1 and 3, thereby implementing a joint motion of the ankle.

FIG. 4 shows the state in which a portion of the distal end of the tibia 93 of a left leg is resected for implantation of a tibia implant 3 and a fibula 99 located outside the same. The distal end of the tibia 93 is resected to have two resected surfaces, such as a medial resected surface 9331a and an intermediate resected surface 9335a, so as to be coupled to a medial surface 315 and a contact surface 313 of the tibial implant 3, which will be described later. As will be described later, the respective surfaces of the tibial implant 3 can be seen in FIGS. 6 and 15.

However, the resected surfaces and the shape of the implant according thereto are only an embodiment of the present disclosure, and the present disclosure also includes an embodiment of an implant in which the distal end of the tibia 93 is resected to have three resected surfaces, such as a medial resected surface 9331a, a lateral resected surface (not shown), and an intermediate resected surface 9335a, according to the shape of the tibial implant so as to be coupled to a medial surface 315, a lateral surface 317, and a contact surface 313 of the tibial implant, respectively. In this case, the lateral surface 317 of the tibial implant 3 is preferably formed in a plane rather than a curved surface.

Next, an artificial ankle joint system coupled to the tibial implant 3 to implement a joint motion of the ankle and a principle thereof will be briefly described with reference to FIG. 5.

An insert 5 made of plastic, such as polyethylene or the like, and serving as a bearing is positioned on the talus implant 1, and the talus implant 1 slides back and forth along the curvature of the lower surface of the insert 5 by an ankle motion, thereby implementing joint motions corresponding to dorsiflexion and plantar flexion motions. A tibial implant 3, which is coupled to a distal end 933 of the tibia 93 and supports the load of the tibia 93, is positioned on the insert 5. The tibial implant 3 may be a fixed type in which the tibial implant 3 is totally fixed to the insert 5, may be a semi-fixed type in which the tibial implant 3 and the insert 5 partially restrict each other to allow a limited relative motion, or may be a free type in which the tibial implant 3 is capable of free movement.

A combination of two or three components described above performs a joint motion in place of the ankle.

Next, the tibial implant 3 according to the present disclosure will be described with reference to FIGS. 6 to 14.

Referring to FIG. 6, the tibial implant 3 according to the present disclosure may include a body part 31, a fixing part 33 extending from one side of the body part 31, spikes 35 extending from the opposite side of the body part 31, and a blocking part 37 formed at the posterior of the body 31.

Referring to FIGS. 6 and 11, the body part 31 may include a joint surface 311 in contact with the insert 5 toward the joint, a contact surface 313 in contact with the intermediate resected surface 9335a of the tibia 93, a medial surface 315 in contact with the medial resected surface 9331a of tibia 93, a lateral surface 317 facing the fibula 99, an anterior boundary surface 318 directed forward, and a posterior boundary surface 319 directed backward.

The joint surface 311 is a bottom surface of the tibial implant 3 and comes into contact with the top surface of the insert 5. In the case of a fixed-type artificial ankle joint, the tibial implant 3 and the insert 5 are integrated, so that the joint surface 311 and the top surface of the insert 5 are completely coupled to each other.

The contact surface 313 is an upper surface opposite the joint surface 311 and comes into contact with an intermediate resected surface 9335a obtained by cutting one side of the distal end 933 of the tibia 93, thereby replacing a portion of the tibia 93. Therefore, the intermediate resected surface 9335a of the tibia 93 is preferably resected into a shape complementary to the contact surface 313 of the tibial implant 3. In addition, the fixing part 33 may be formed at one side of the contact surface 313, and, preferably, may be located at an anterior side on the contact surface 313. When the contact surface 313 comes into contact with the intermediate resected surface 9335a of the tibia 93, the fixing part 33 penetrates the same to strengthen the fixing force, which will be described in more detail later.

The medial surface 315 is coupled to the medial resected surface 9331a of the tibia 93 as shown in FIG. 15. To this end, the medial surface 315 may have a shape complementary to the medial resected surface 9331a, and may be preferably formed as a plane for the convenience of cutting the tibia 93.

As shown in FIG. 6, the lateral surface 317 is positioned on the lateral side of the ankle. In the case where the tibia 93 has only two resected surfaces 9331a and 9335a as described above, the lateral surface 317 may be recessed inwardly to be concave. However, in the case where the tibia 93 has three resected surfaces 9331a, 9333a, and 9335a, the lateral surface 317 may be configured as a plane.

The anterior boundary surface 318 is directed toward the front of the ankle, and the posterior boundary surface 319 is directed toward the posterior of the ankle.

Referring to FIGS. 6 and 7, the fixing part 33 may include an axis 331, as a center thereof, and wings 333 extending a predetermined length from the axis 331. At this time, the fixing part 33 including the axis 331 and the wings 333 may be configured as a single body, thereby preventing bone resorption due to the stress shielding effect. In addition, such a structure increases the amount of preserved bone and facilitates an operation when performing revision arthroplasty, compared to the prior art in which the bone located between two or more pegs is removed together the implant, thereby increasing the amount of resected bone.

The fixing part 33 may be formed at the anterior side of the contact surface 313 so as to facilitate insertion thereof into the tibia 93. In addition, unlike the prior art, since only a single fixing part 33 is provided, it is preferable to position the fixing part 33 in the center with respect to the left and right sides of the contact surface 313 in consideration of even distribution of stress and load support. However, the position of the fixing part is not limited thereto, and may be varied because it is not a core feature of the disclosure.

Referring to FIG. 10, the fixing part 33 may extend a predetermined length upwards at a predetermined angle (θ) with the line perpendicular to the contact surface 313 toward the posterior thereof. The ankle joint is smaller than a knee joint or a hip joint. In addition, the plantar flexion of the ankle joint has a limited range of motion compared to the knee joint. Therefore, in the artificial ankle joint arthroplasty using an anterior approaching method, the incision site is narrow, which makes it difficult to check the resected surfaces of the tibia 93 and to insert the implant thereinto. Therefore, in order to push and insert the implant into a narrow incision site from the front, it is preferable to configure the fixing part 33 in the form inclined backward, thereby enabling natural insertion.

With reference to FIGS. 6 and 7, the axis or central portion 331 constitutes the center of the fixing part 33 and provides a function of connecting the wings 333 to each other to maintain. At this time, a portion that is exposed to the outside is referred to as a "top end" or "end face" 331a. However, there may be another embodiment in which the wings 333 are directly connected to each other, excluding the element called an "axis" or "central portion". In the illustrated embodiment, each wing 333 incldues a front face 360 and an opposing back face 362 that outwardly project from the contact surface 313 to a top edge 364 and that laterally project from the central portion 331 to a side edge 366. Top edge 364 and side edge 366 of each wing 333 join together at a corner 368 that is spaced apart from the central portion 331. As depicted, end face 331a of central portion 331 can be flattened. As further depicted, top edge 364 of each wing 333 can project laterally outward from end face 331a of central portion 331.

Referring to FIG. 8, the wings 333 may be configured to extend in different directions with respect to the center of the axis 331 or the fixing part 33, and, preferably, four wings may be provided. More preferably, the four wings may be arranged at an interval of 90 degrees with each other, thereby efficiently distributing the stress. However, the four wings 333 are not necessarily provided, and, according to another embodiment, only one or more posterior wings may be provided as claimed in the claims. Here, the posterior wing indicates the wing located behind an ML line, which will be described below.

In FIG. 8, "w" represents the width of the wing 333, and "L" represents the length of the wing 333, which will be described in detail later.

Referring to FIGS. 7 and 8, there are an ML line that extends in a medial and lateral direction while passing through the center of the fixing part 33 and an AP line that extends in an anterior and posterior direction of the tibial implant 3 while passing through the center of the fixing part 33. At this time, the wings 333 may extend at a predetermined angle (Φ) with respect to the AP line, and, in this case, since two wings 333 are directed backward, it is possible to prevent the concentration of stress on one side of the wings.

Referring to FIG. 14 illustrating another embodiment of the present disclosure, four wings 333 are configured in the form of a cross (+), instead of an X shape, with respect to the front and rear of the tibial implant 3. However, the fixing part 33 extends backward at a predetermined angle as described above, if the fixing part 33 has a cross (+) form, the load acts downwards in a straight position, so that the stress is concentrated on the portion C. If the stress is concentrated on only one side as described above, the fixing part may be broken by repeated use.

However, if the four wings are arranged in an X shape as shown in FIG. 8, even if the fixing part 33 is inclined backward, the stress is dispersed through the lower ends of the two wings, thereby lowering the possibility of fracture. At this time, the two posterior wings may be arranged to be symmetrical with respect to the AP line, and the anterior wings may be arranged to be symmetrical with the posterior wings with respect to the ML line, thereby configuring an X form overall. The four wings 333 may be referred to as an "anterior medial wing" 3331, an "anterior lateral wing" 3333, a "posterior medial wing" 3335, and a "posterior lateral wing" 3337, respectively.

The fixing part 33 may have a tapered shape in which the cross-sectional area thereof is reduced as it goes from the contact surface 313 to the top end 331a.

More specifically, referring to FIG. 10, the length (L) of the anterior lateral wing 3333 may be reduced as it goes from the contact surface 313 to the top end 331a. That is, $L_2$ is greater than $L_1$. With this configuration, the distance between two neighboring wings (e.g., the anterior lateral wing 3333 and the posterior lateral wing 3337 in the case of FIG. 10) becomes smaller as it goes upwards, so that the angle (α) formed between the two wings 3333 and 3337 exceeds zero. This is intended to easily insert the tibial implant 3 into the intermediate resected surface 9335a of the tibia 93 while securing a sufficient fixing force. This can also be confirmed in the anterior medial wing 3331 shown in FIG. 11 in which $L_2'$ is greater than $L_1'$ and an angle (β) between the two wings 3331 and 3333 is greater than zero. In addition, the remaining wings, which are not shown, may be formed in the same manner.

Referring to FIG. 12, it can be seen that the anterior lateral wing 3333 has a tapered shape in the vertical direction in which the width (w) thereof is reduced as it goes from the contact surface 313 to the top end 331a. That is, $w_2$ is configured to be greater than $w_1$. Therefore, the angle (γ) formed between both sides of the wing 333 has a value greater than zero. This is intended to easily insert the tibial implant 3 into the intermediate resected surface 9335a of the tibia 93 while securing a sufficient fixing force. This can also be confirmed in the posterior lateral wing 3337 shown in FIG. 13 in which $w2'$ is greater than $w1'$ and a value δ is greater than zero. In addition, the remaining wings, which are not shown, may be formed in the same manner.

According to the above configuration, the side surface 333a of the fixing part 33 illustrated in FIGS. 9 to 11 may be a surface inclined from the contact surface 313 to the top end 331a.

The side surface 333a may be configured to meet the contact surface 313 at a specific angle, or may be connected with the contact surface 313 so as to form a gentle curved surface as shown in the portion "e" in FIGS. 12 and 13. When the tibial implant 3 is used after implantation into a body, if a load by weight is applied thereto, the force is concentrated on the connection portion of the side surface 333a and the contact surface 313. The above configuration is intended to prevent the connection portion from being broken by the stress generated due to the concentration of the force. If the connecting portion is formed as a curved surface as shown in the portion "e" in FIGS. 12 and 13, it is more robust than the connection portion formed at a right angle, thereby increasing the life span of the artificial ankle joint.

In addition, a portion where the side surface 333a meets the top end 331a may also be formed to be a gentle curved surface, such as a portion "f" in FIGS. 12 and 13. This is intended to prevent the stress from being concentrated on one side to be broken while facilitating insertion of the implant 3 into the bone.

In addition, as shown in a portion "d" in FIG. 8, the width (w) of each wing 333 may increase as it goes to from the outside to the axis 331, so that the neighboring wings meet each other at lateral sides thereof. At this time, the portion in which the two neighboring wings meet may be formed in a gentle curved surface. According to the above configuration, the side surface 333a may be formed in a curved surface without any angled portions.

The spikes 35 may include a first spike 351, a second spike 353, and a third spike 355. As shown in FIG. 6, the three spikes 351, 353, and 355 may all have the same shape. Here, a description will be made on the basis of the first spike 351.

The first spike 351 has a horn shape for easy insertion into the resected surface 9335a of the tibia 93, and may have a shape of a triangular pyramid, a cone, or the like, as well as a quadrangular pyramid as shown in FIG. 6.

In addition, the portion where the first spike 351 meets the contact surface 313 may be formed as a gentle curved surface, and may include a boundary surface connecting the first spike 351 and the contact surface 313.

The boundary surface is a portion which is a boundary with respect to the contact surface 313 and is formed as a gentle curved surface. In addition, if the first spike 351 and the contact surface 313 are connected using the boundary surface, it is possible to support the load of a human body and to distribute the stress, thereby preventing a fracture.

Referring to FIG. 10, the blocking part 37 is configured to extend a predetermined length upwards from the posterior of the body part 31, and preferably extends in the form of a thin wall along the posterior boundary surface 319. The blocking part 37 completely covers the posterior of the intermediate resected surface 9335a of the tibia 93 (see FIG. 15) while extending a predetermined length toward the proximal end of the tibia 93 when performing artificial ankle joint arthroplasty. Accordingly, it is possible to prevent a bone from growing from the resected surface 9335a or the like and extending downwards to lead to the talus 91 due to heterotopic ossification after an operation.

In addition, the blocking part 37 may include an medial surface 371 facing the fixing part 33, and the medial surface 371 comes into close contact with the posterior surface (not shown) of the tibia 93 when performing artificial ankle joint arthroplasty, thereby preventing a bone from growing from the resected surface 9335a.

Next, a description will be made of a process in which the tibial implant 3 according to the present disclosure is inserted and coupled to the tibia 93 on the basis of the above-described configuration and coupling relationship.

Referring to FIG. 15, the distal end of the tibia 93 is cut into two resected surfaces 9331a and 9335a for implantation of the tibial implant 3, and then the tibial implant 3 is inserted from bottom to top to be coupled such that the medial surface 315 comes into contact with the medial resected surface 9311a. At this time, the fixing part 33 is inserted into the inside of the tibia 93 to sufficiently secure the initial fixing force and avoid the stress shielding effect, thereby preventing bone resorption.

In addition, it is possible to facilitate an operation by increasing the amount of bone to be preserved when performing revision arthroplasty. Further, the blocking part 37 comes into close contact with the posterior surface (not shown) of the tibia 93 to prevent the occurrence of heterotopic ossification in which a bone grows from the resected surface 9335a. Accordingly, the life span of the artificial joint can be increased and the pain of the patient can be alleviated.

Although the description of the configuration, the coupling relationship, and the coupling process has been made above on the basis of an implant inserted into the tibia 93 in artificial ankle joint arthroplasty, this is only an embodiment of the present disclosure, and the present disclosure may also be applied to an implant inserted into another bone. For example, the present disclosure may be applied to a talus implant coupled to a talus or an implant used for an artificial knee joint, an artificial hip joint, an artificial shoulder joint, or the like.

The above detailed description illustrates an example of the present disclosure. In addition, the above description relates to a preferred embodiment of the present disclosure, and the present disclosure may be used in various other combinations, modifications, and environments. That is, the present disclosure may be changed or modified within the scope of the concept of the disclosure disclosed in the present specification, the scope equivalent to the disclosed content, and/or the scope or knowledge of the art. The above-described embodiment illustrates the best mode for carrying out the technical idea of the present disclosure, and various modifications required for a specific application field and usage of the present disclosure are possible. Therefore, the detailed description of the disclosure above is not intended to limit the present disclosure to the disclosed embodiment. Further, the appended claims must be construed to encompass other embodiments.

What is claimed is:

1. A tibial component for coupling to a tibia in artificial ankle joint arthroplasty, the tibial component comprising:
   a body part having a contact surface configured to contact a resected surface of a distal end of the tibia, a joint surface opposite the contact surface, and a medial surface extending between the contact surface and the joint surface and configured to contact another resected surface of the tibia, the body part including an anterior-posterior line and a medial-lateral line that extends orthogonal to the anterior-posterior line;
   at least one spike outwardly projecting from the contact surface at a posterior side of the contact surface; and
   a fixing part extending a predetermined length outward from the contact surface, the fixing part comprising:
      a central portion outwardly projecting from the contact surface and terminating at an end face;
      two posterior wings extending at angles symmetrical to each other relative to the anterior-posterior line; and
      two anterior wings extending at angles symmetrical with the posterior wings relative to the medial-lateral line;
   the two posterior wings and the two anterior wings extending in an X-shape from the central portion of the fixing part,
   wherein the fixing part is disposed anterior to the at least one spike and extends at an angle toward the posterior side of the contact surface,
   wherein the two anterior wings and the two posterior wings each taper inwardly as they extend from the contact surface to a top end of the fixing part so that a cross-sectional area of the fixing part is reduced as the fixing part extends from the contact surface to the top end of the fixing part;
   wherein the contact surface has an anterior side opposite of the posterior side, the anterior side terminating at an anterior boundary surface that extends between the contact surface and the joint surface, wherein the contact surface extending between the fixing part and the anterior boundary surface is planar with no projections upstanding therefrom; and
   further comprising a blocking part upstanding from the contact surface so that the at least one spike is disposed between fixing part and the blocking part, the blocking part having an elongated length at least partially extending between the medial surface and an opposing lateral surface of the body part.

2. The tibial component according to claim 1, wherein each of the two anterior wings extends to form an angle of 90 degrees with each of the two posterior wings adjacent thereto.

3. The tibial component according to claim 1, wherein at least one wing from the two anterior wings and the two posterior wings has a front face and an opposing back face with a width extending therebetween, the width tapering in a vertical direction extending from the contact surface to the top end of the fixing part, such that the width of the at least one wing is reduced from the contact surface to a top end of the at least one wing.

4. The tibial component according to claim 1, wherein a lower part of a side surface of the fixing part forms a curved surface connecting to the contact surface to support a load and distribute stress.

5. The tibial component according to claim 4, wherein an upper part of the side surface of the fixing part forms a curved surface connecting to the top end of the fixing part to facilitate insertion of the fixing part into the tibia.

6. The tibial component according to claim 5, wherein a portion of the side surface of the fixing part in which two neighboring wings of the two anterior wings and the two posterior wings meet forms a curved surface to enable a natural connection and support the load.

7. The tibial component according to claim 1, wherein the at least one spike is in a form of a horn.

8. The tibial component according to claim 7, wherein a boundary portion between the at least one spike and the contact surface has a boundary surface connecting the at least one spike and the contact surface, said boundary surface being curved.

9. The tibial component according to claim 1, wherein a lateral surface of the tibial component is formed to be a concave curved surface.

10. The tibial component according to claim 1, wherein the blocking part extends a predetermined length in the vertical direction from the posterior side of the body part.

11. The tibial component according to claim 10, wherein the blocking part is formed along a posterior boundary surface of the body part to prevent heterotopic ossification.

12. The tibial component according to claim 1, wherein each of the posterior wings and the anterior wings includes a front face and an opposing back face that outwardly project from the contact surface to a top edge and that laterally projects from the central portion to a side edge, the top edge and side edge of each wing intersecting at a corner that is spaced apart from the central portion.

13. The tibial component according to claim 12, wherein the top edge of each wing projects laterally outward from the end face of the central portion.

14. The tibial component according to claim 1, wherein the end face of the central portion is flattened.

15. The tibial component according to claim 1, wherein the at least one spike comprises a plurality of spaced apart spikes each extending a predetermined length outward from the contact surface, the predetermined length of the plurality of spaced apart spikes being shorter than the predetermined length of the fixing part.

16. The tibial component according to claim 15, wherein the fixing part is centrally disposed between the medial surface and an opposing lateral surface of the body part.

17. The tibial component according to claim 15, wherein each of the plurality of spikes orthogonally outwardly project from the contact surface.

18. The tibial component according to claim 1, wherein the posterior side of the contact surface terminates at a posterior boundary surface that extends between the contact surface and the joint surface, wherein the blocking part upstands along the posterior boundary surface.

* * * * *